US007285130B2

United States Patent
Austin

(10) Patent No.: US 7,285,130 B2
(45) Date of Patent: Oct. 23, 2007

(54) STENT DELIVERY SYSTEM

(75) Inventor: Michael Austin, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 461 days.

(21) Appl. No.: 10/832,619

(22) Filed: Apr. 27, 2004

(65) Prior Publication Data
US 2005/0240254 A1 Oct. 27, 2005

(51) Int. Cl.
*A61F 2/82* (2006.01)
(52) U.S. Cl. .................... 623/1.12; 623/1.11; 623/1.42
(58) Field of Classification Search ............. 623/1.11, 623/1.12; 606/108, 194
See application file for complete search history.

(56) References Cited

U.S. PATENT DOCUMENTS

| | | | |
|---|---|---|---|
| 5,662,703 A * | 9/1997 | Yurek et al. ............... | 623/1.12 |
| 5,681,345 A | 10/1997 | Euteneuer .................. | 623/1.11 |
| 5,788,707 A | 8/1998 | Del Torot et al. ......... | 623/1.11 |
| 6,066,155 A | 5/2000 | Amann et al. .............. | 606/192 |
| 6,096,045 A | 8/2000 | Del Toro et al. ........... | 606/108 |
| 6,221,097 B1 | 4/2001 | Wang et al. ................ | 623/1.11 |
| 6,254,628 B1 * | 7/2001 | Wallace et al. ............ | 623/1.12 |
| 6,331,186 B1 | 12/2001 | Wang et al. ................ | 623/1.11 |
| 6,342,066 B1 | 1/2002 | Toro et al. .................. | 623/1.11 |
| 6,350,277 B1 | 2/2002 | Kocur ........................ | 623/1.11 |
| 6,391,050 B1 * | 5/2002 | Broome ..................... | 623/1.11 |
| 6,443,880 B2 | 9/2002 | Blais et al. .................. | 492/16 |
| 6,478,814 B2 | 11/2002 | Wang et al. ................ | 623/1.12 |
| 6,544,278 B1 | 4/2003 | Vrba et al. .................. | 606/198 |
| 6,562,063 B1 | 5/2003 | Euteneuer et al. ......... | 623/1.12 |
| 6,607,552 B1 | 8/2003 | Hanson ..................... | 623/1.11 |
| 6,645,238 B2 * | 11/2003 | Smith ........................ | 623/1.11 |

FOREIGN PATENT DOCUMENTS

| WO | WO 96/32078 | 10/1996 |
|---|---|---|
| WO | WO 02/38084 A2 | 5/2002 |

* cited by examiner

*Primary Examiner*—Glenn K. Dawson
(74) *Attorney, Agent, or Firm*—Vidas, Arrett, Steinkraus

(57) ABSTRACT

A medical device for delivery of a self-expanding stent comprises a catheter assembly having a catheter shaft and a self-expanding stent disposed thereabout. A retractable sheath is disposed about the catheter shaft and the stent. The retractable sheath retains the stent in a reduced diameter condition prior to delivery. A retractable membrane is also disposed about the catheter shaft and the stent prior to delivery. Prior to delivery a first portion of the membrane is positioned between the stent and the retractable sheath. A second portion of the retractable membrane extends from the first portion and is positioned radially external of the retractable sheath. The retractable sheath and the retractable membrane are independently moveable relative to one another.

20 Claims, 11 Drawing Sheets

STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to catheters and catheter assemblies for use in medical procedures. More specifically, this invention relates to a stent delivery catheter system, such as the kind used in percutaneous transluminal coronary angioplasty (PTCA) procedures, for the delivery of a stent into a body lumen.

2. Description of the Related Art

Percutaneous transluminal coronary angioplasty (PTCA) is a procedure which is well established for the treatment of blockages, lesions, stenosis, thrombus, etc. present in body lumens such as the coronary arteries and/or other vessels.

A widely used form of percutaneous coronary angioplasty makes use of a dilation balloon catheter which is introduced into and advanced through a lumen or body vessel until the distal end thereof is at a desired location in the vasculature. Once in position across a afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. Nos. 5,681,345; 5,788,707; 6,066,155; 6,096,045; 6,221,097; 6,331,186; 6,342,066; 6,350,277; 6,443,880; 6,478,814 and U.S. patent application Ser. No. 09/664268 entitled Rolling Socks and filed Sep. 18, 2000.

It is known that in some stent delivery systems, such as those having pull back sheathes which retain a self-expanding stent having a therapeutic coating on the catheter prior to delivery, the self-expanding stent will tend to exert an outwardly acting radial force against the sheath. During retraction of the sheath to release the stent, the frictional interaction between the sheath and stent may detrimentally affect the coating on the stent. Such interaction may lead to damage of the coating, particularly when the stent is remains enclosed by the sheath in the pre-delivery state for extended periods.

The present invention seeks to address these and/or other problems by providing catheter assemblies with a variety of embodiments and features which improve stent retention and deployment characteristics.

All U.S. patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, in at least one embodiment the invention is directed to a stent delivery catheter wherein prior to delivery of the stent the stent is disposed about a stent receiving region of the inner shaft of the delivery catheter, and a retractable retaining sheath or outer shaft is disposed about the stent. The catheter is also equipped with a retractable membrane that is wrapped around the distal region of the retaining sheath. A first end of the retractable membrane is secured to the inner shaft of the catheter proximal of the stent receiving region and extends distally between the stent and retaining sheath. At the distal end of the retaining sheath the membrane folds over the retaining sheath and extends proximally to where its second end is secured to an actuation sheath or member. The actuation sheath is slidable relative to the retaining sheath.

To deliver the stent a retraction mechanism such as a screw or lever assembly retracts both the retaining sheath and the actuation sheath. The retracting actuation sheath pulls the membrane proximally over the retracting retaining sheath and exposes the stent for delivery.

In at least one embodiment the stent to be delivered is a self-expanding stent having one or more therapeutic coatings thereon. A therapeutic coating may be any of a variety of substances including one or more drugs, carriers, or other substances which are desired to be transported and delivered to a site within a body lumen.

In at least one embodiment the membrane is constructed of one or more materials which limits or prevents contact bonding between the membrane and the stent and/or the therapeutic coating on the stent. In some embodiments one or more lubricious substances be applied to the stent and/or membrane to aid in the prevention of pressure contact bonding and/or to encourage ease of retraction of the membrane from the sheath.

In at least one embodiment, at least the portion of the membrane disposed about the stent prior to delivery is a substantially tubular sleeve of membrane material. Distal of the stent, the sleeve separates into about 3 to about 8 strips of membrane material, which wrap around the distal end of the retaining sheath and extend proximally back over the retaining sheath where they terminate at the actuation sheath.

In at least one embodiment the membrane is at least partially constructed of polyester or polyamide polymers.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
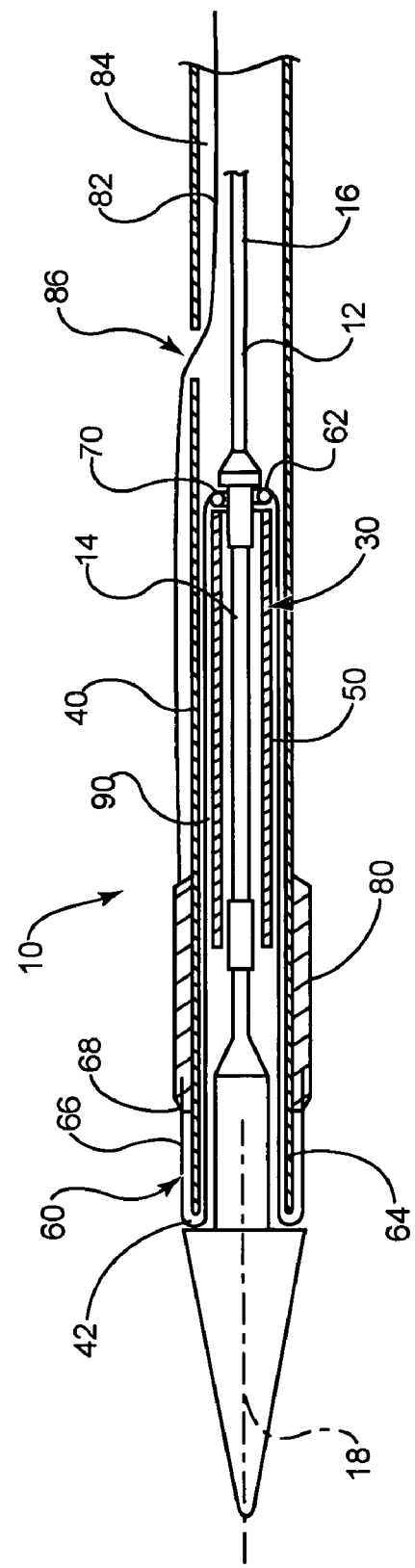
FIG. 1 is a cross-sectional side view of an embodiment of the invention comprising a stent delivery system having a rolling membrane.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
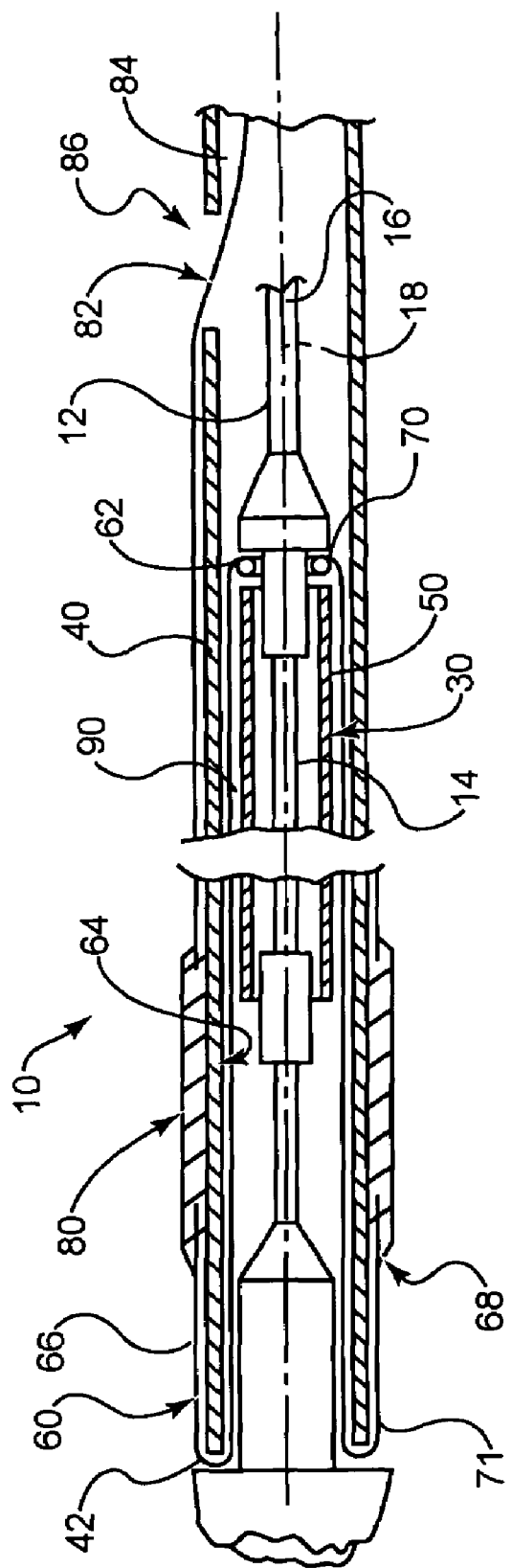
FIG. 2 is a partial enlarged view of the embodiment shown in FIG. 1.

In at least one embodiment, an example of which is shown in FIGS. 1-2, a stent delivery system is shown comprising a catheter 10 which is configured to deliver a self-expanding stent 30.

Catheter 10 includes a inner shaft 12, a portion of which defines a stent receiving region 14. Inner shaft 12 may further define a guidewire lumen 16 through which a guidewire 18 may be passed in order to advance the catheter to a predetermined position in a body lumen or vessel. Alternatively, the shaft 12 may be configured as a push catheter without the need for guidewire 18 and/or lumen 16.

Prior to delivery the stent 30 is disposed about the stent receiving region 14 of the inner shaft 12. Stent 30 is preferably a self-expanding or hybrid expandable stent. In some embodiments the stent may be at least partially constructed from a one or more of the following shape memory materials: nitinol, shape-memory polymer(s), FeMnSiCrNi shape-memory stainless steel, etc., but may include other material or materials as well. In some embodiments the stent includes one or more areas, bands, coatings, members etc. that is (are) detectable by imaging modalities such as X-Ray, MRI or ultrasound. In some embodiments at least a portion of the stent 30 is at least partially radiopaque.

In some embodiments the stent 30 may include one or more therapeutic and/or lubricious coatings 50 applied thereto.

A therapeutic agent may be placed on the stent in the form of a coating 50. In at least one embodiment the coating 50 includes at least one therapeutic agent and at least one polymer.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetyl-salicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vasoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are $Lin^-$, $Sca-1^+$, $c-Kit^+$, $CD43^+$, $CD45^+$, $CD34^-$ $Lin^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

$Lin^-CD34^-$—Although $CD34^+$ cells have received much attention, many articles have been published lately which suggest the most primitive bone marrow derived stem cells are $CD34^-$ $Lin^-CD34^+$—Presence of the cell surface protein CD34 has been used to identify hematopoietic stem cells. However, the marker is also present on progenitor cells and white blood cells of various levels of maturity.

$Lin^-cKit^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord blood cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the $6^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene-oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In at least one embodiment an example of a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups.

Preferred polyolefinic blocks include polymeric blocks of isobutylene,

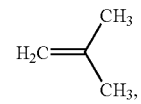

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

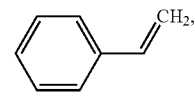

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures.

Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) $B(AB)_n$ or $A(BA)_n$ (linear alternating block), or (d) $X-(AB)_n$ or $X-(BA)_n$ (includes diblock, triblock and other radial block copolymers), where n is a positive whole number and X is a starting seed, or initiator, molecule. One specific group of polymers have $X-(AB)_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Figure 5:
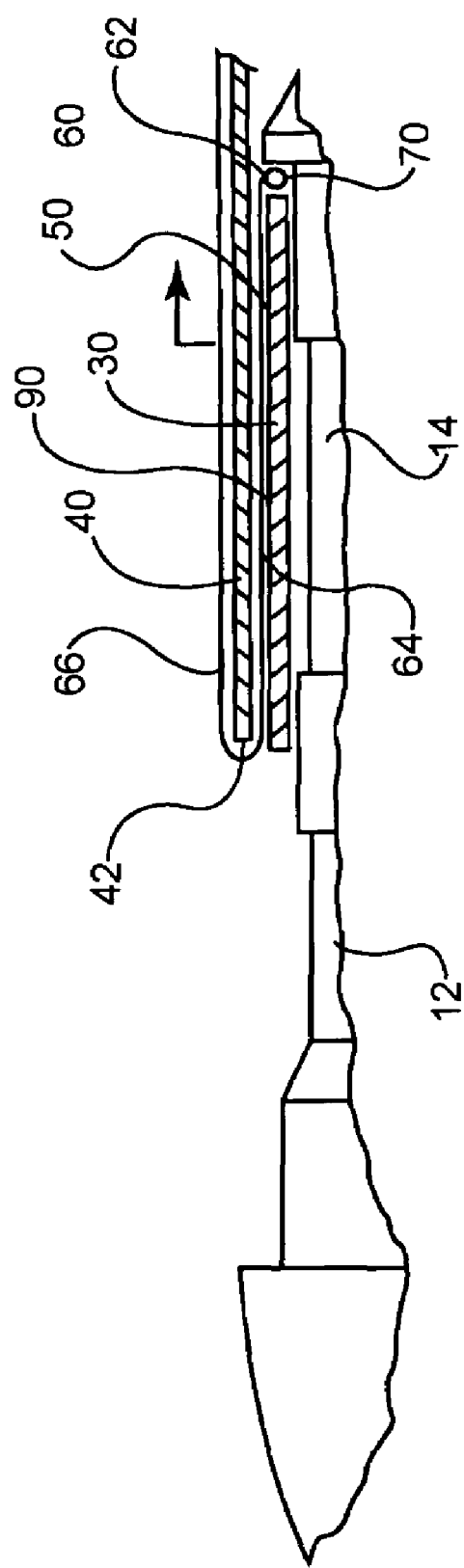
FIG. 5 is a partial enlarged view of the embodiment shown in FIG. 1 depicted during retraction of the membrane and sheath subsequent to the depiction in FIG. 4.
Figure 6:
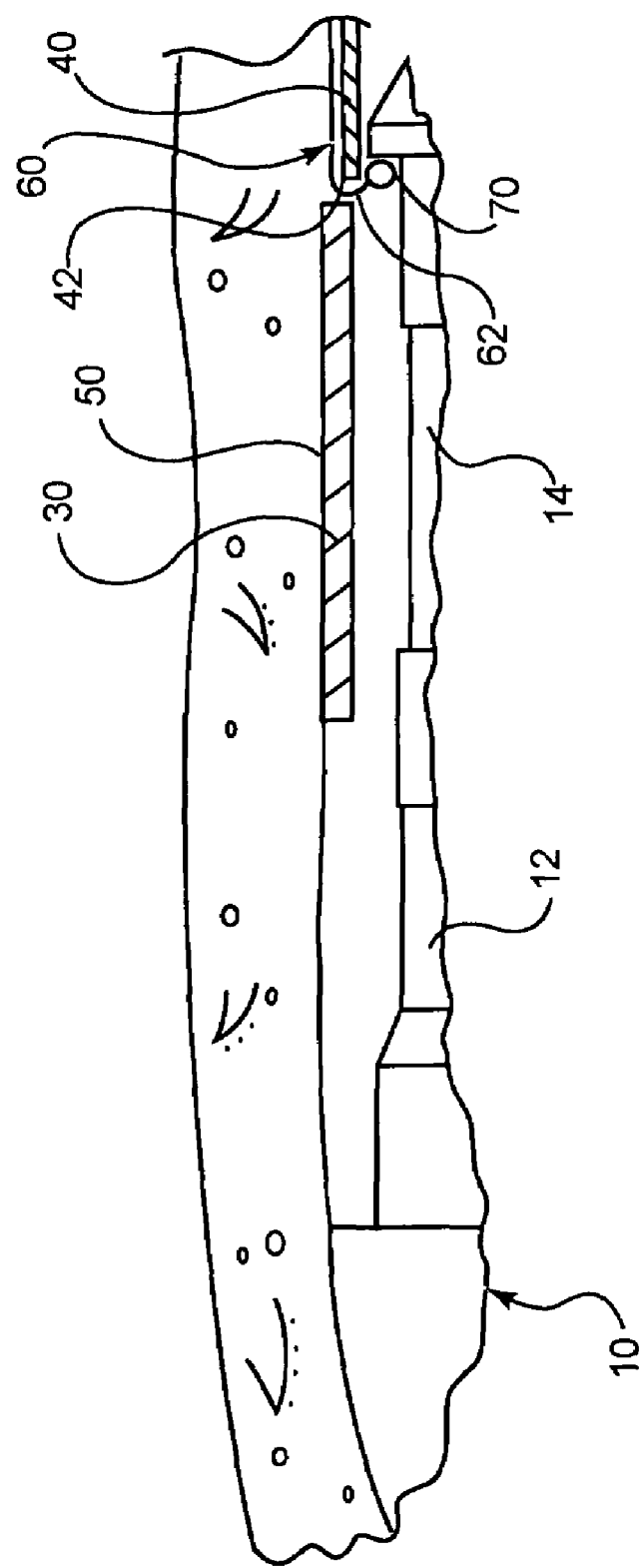
FIG. 6 is a partial enlarged view of the embodiment shown in FIG. 1 wherein the membrane and sheath are fully retracted and the stent is deployed within a body lumen.

In the various embodiments described herein the stent 30 is preferably configured to be at least partially self-expanding or have self-expanding characteristics. As used herein the term "self-expanding" refers to the tendency of the stent to return to a preprogrammed diameter when unrestrained from the catheter, such as in the manner depicted in FIGS. 5-6 In the present embodiment when the stent is disposed about the stent receiving region 14 of the inner shaft 12, the stent is restrained in its reduced diameter or pre-delivery configuration by a retractable retaining sheath 40 which is disposed about the entire length of the stent 30 prior to delivery.

The retaining sheath 40 is disposed about the stent 30 prior to delivery. The retaining sheath 40 has sufficient hoop strength to retain the stent in its pre-delivery or reduced diameter state. Disposed between the stent 30 and the retaining sheath 40 is a portion of a retractable membrane 60. The position of the retractable membrane 60 between the stent 30 and the retaining sheath 40 ensures that the stent 30, and more particular any therapeutic coating 50 present on the stent 30 does not come into contact with the retractable sheath 40 prior to, during or subsequent to delivery.

A first end 62 of the membrane 60 is engaged to the inner shaft 12 of the catheter 10 at a region proximally adjacent to the stent receiving region 14. The first end 62 is fixedly engaged to the inner shaft 12 by a retention ring 70. Ring 70 may be an annular member disposed about the first end 62 of the membrane 60 to provide a mechanical interface between the membrane and the inner shaft 12. Alternatively, ring 70 may be a weld or bond between the shaft 12 and the membrane 60 or any other mechanism for engaging the membrane 60 and inner shaft 12.

The membrane 60 may be characterized as having an inner region 64 and an outer region 66. As depicted in the various figures included herewith, the inner region 64 of the membrane 60 extends distally from the retention ring 70 to the distal end 42 of the retaining sheath 40. At the distal end 42 of the sheath 40 the membrane 60 passes out from under the retaining sheath 40 and wraps around the distal end 42 of the retaining sheath 40. From the distal end 42 of the retaining sheath 40 the outer region 66 of the membrane 60 extends proximally from the inner region 64. The outer region 66 extends to a second end 68 of the membrane 60 which terminates and/or is engaged to a retraction member or collar 80.

In some embodiments the retaining sheath 40 may be 7 French diameter with an outer diameter of about 2-3 mm, an inner diameter of about 1-2 mm and a wall thickness less than 1 mm. In at least one embodiment the sheath 40 has an outer diameter of about 2.337 mm and an inner diameter of about 1.981 mm, and has a wall thickness of about 0.178 mm. The membrane 60 is typically about 0.01 mm to about 0.05 mm thick. In at least one embodiment the membrane 60 is about 0.013 mm to about 0.025 mm thick (0.0005" to 0.001"). In at least one embodiment the membrane 60 is about 5 times to about 10 times thinner than the sheath 40.

For effective operation the retraction collar 80 needs to be similar in wall thickness to the sheath 40 in order to form a sufficiently rigid attachment for the membrane 60, and one capable of co-axial, slidable engagement with the retaining sheath 40.

As indicated above, the membrane 60 is a thin, flexible polymer membrane of polyester, polyamide, polyethylene terephalate polyester (PET), crosslinked polyethylene, polyurethane, plasticized PVC (polyvinylchloride), polytetrafluoroethylene (PTFE) and any other polymers and combinations thereof.

The basic materials of the sheath 40 and membrane 60 may be similar for both components. However, in some embodiments the material of the membrane 60 may comprise additional or more plasticizing agents which the polymer of the sheath 40 does not include. In some embodiments one or more polyurethane based polymer is included in the membrane 60 to provide the membrane with elastic properties as this contributes directly to a reduced membrane retraction force.

As is illustrated in the various figures, when the membrane 60 is retracted the membrane is in effect turned completely 'inside-out' as it is pulled back over the sheath 40. As such, the membrane 60 is at least partially constructed of one or more materials capable of providing an amount of elastic deformation sufficient to allow the membrane 60 to be rolled back over the sheath 40 as such an action results in the outer region 66 of the membrane 60 attaining an outermost diameter that is at least slightly larger than the diameter of the inner region 64 as the membrane 60 is rolled back. Accordingly, the mechanism of the rolling membrane 60 also requires a higher sheath retraction force due to the energy needed to expand the continuously rolling portion, and to overcome the frictional drag at the interface of the two tubular membranes at the end 42 of the sheath 40.

Figure 3:
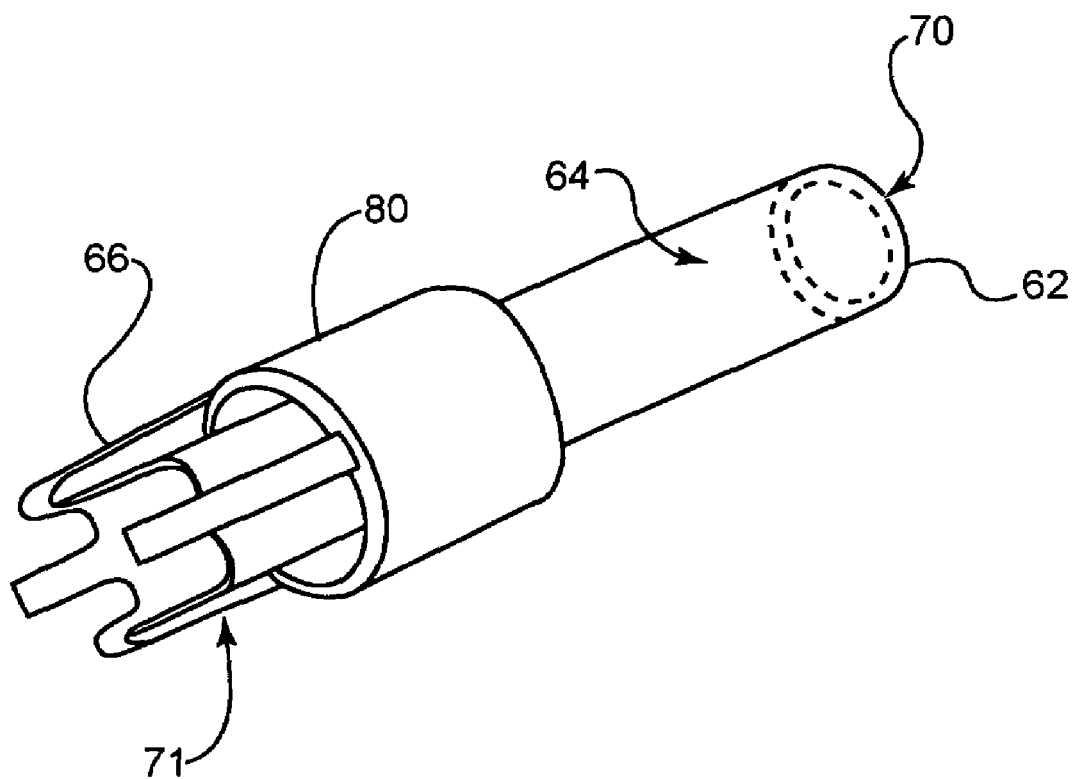
FIG. 3 is a perspective view of the rolling membrane and actuation sheath assembly of the system shown in FIG. 2.

In some embodiments, an example of which is shown in FIG. 3, in order to compensate for the higher forces and frictional drag that the membrane 60 is subjected to, at least a portion of the membrane 60 may comprise a plurality of strips 71 of membrane material which extend from the inner region 64 to the retraction collar 80. The number of strips may vary from about 3 strips to about 8 strips. In at least one embodiment the strips number from about 4 to about 6 strips. As the membrane 60 is retracted, the strips 71 roll, separate, open and turn back more freely in a sharp rolling bend around the sheath 40 than a solid tubular rolling membrane.

The retraction collar 80 is disposed about the retaining sheath 40 and is independently slidable relative thereto. Engagement of the membrane 60 to the retraction collar 80 permits retraction of the membrane 60 from about the stent 30 when the retaining sheath 40 and the membrane retraction collar 80 are pulled proximally relative to the inner shaft 12.

Figure 4:
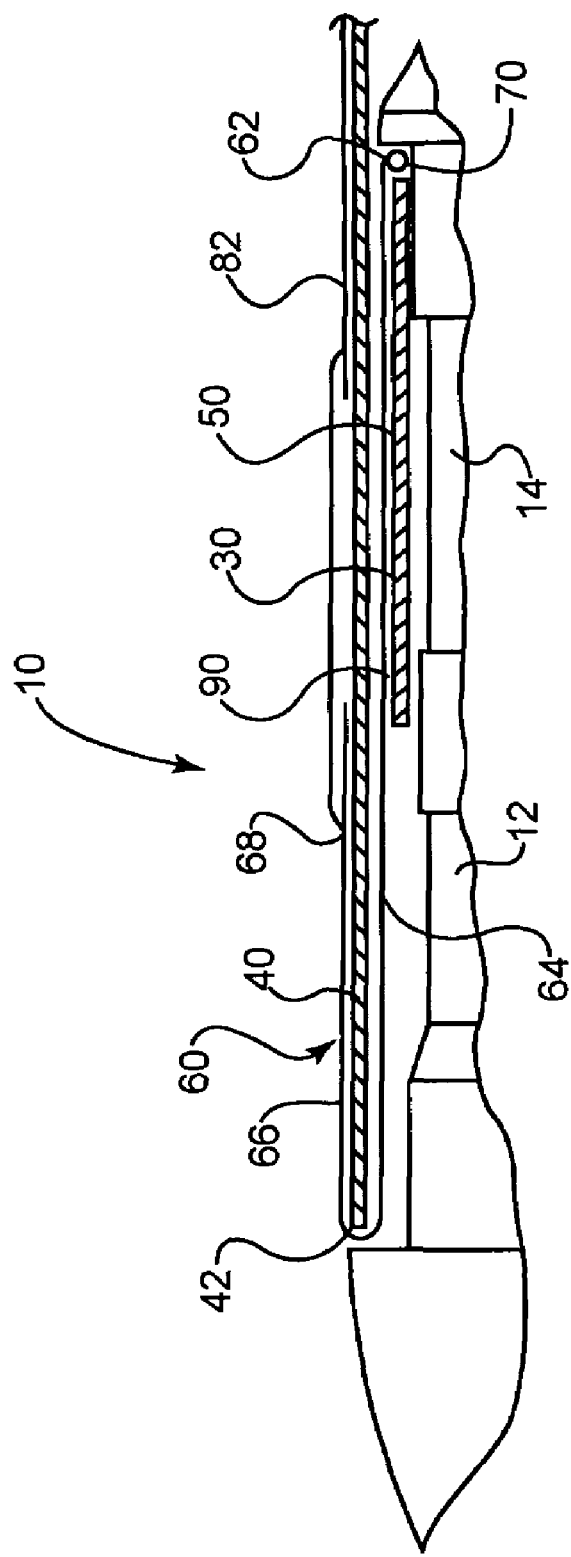
FIG. 4 is a partial enlarged view of the embodiment shown in FIG. 1 depicted during retraction of the membrane and sheath.
Figure 8:
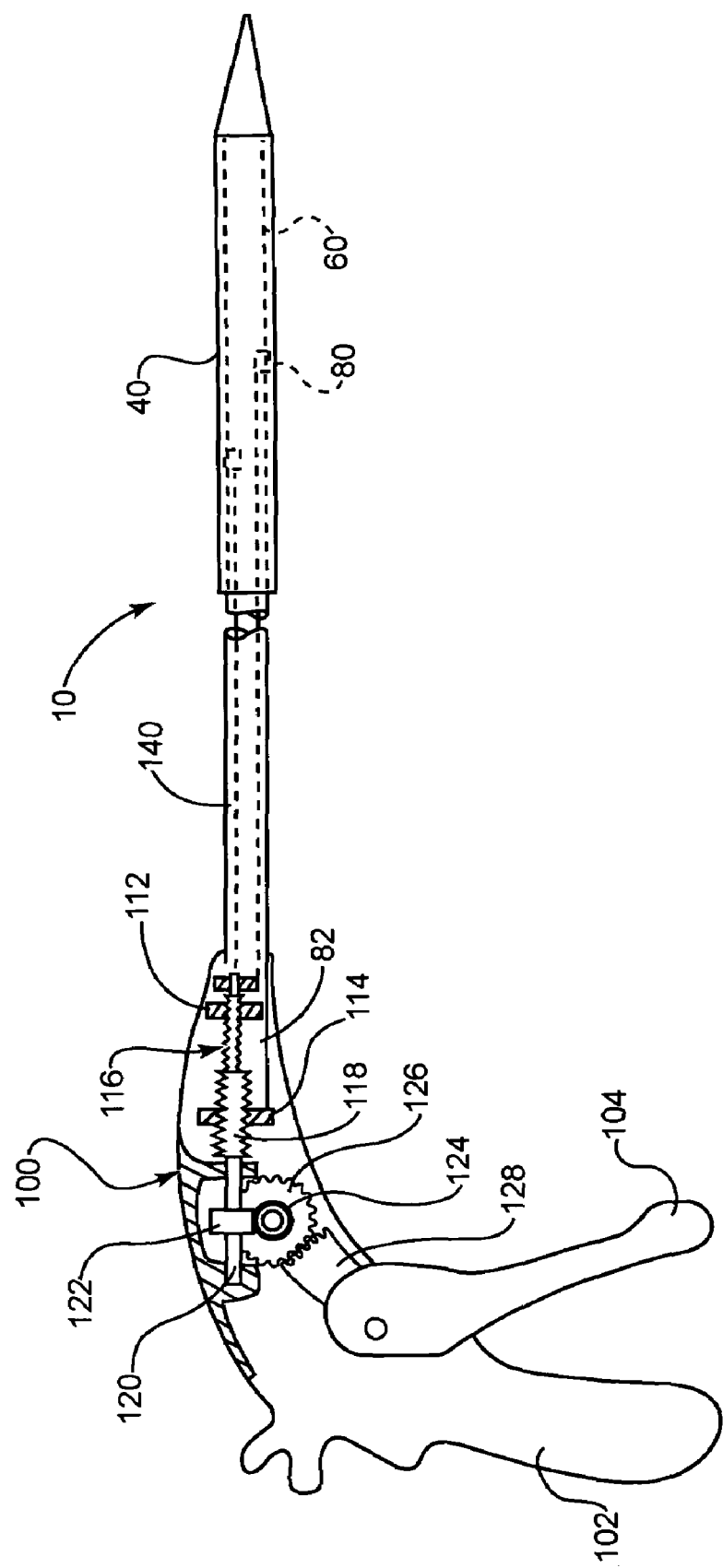
FIG. 8 is a partial cross-sectional side view of an embodiment of the invention showing the proximal and distal portions of the system.
Figure 9:
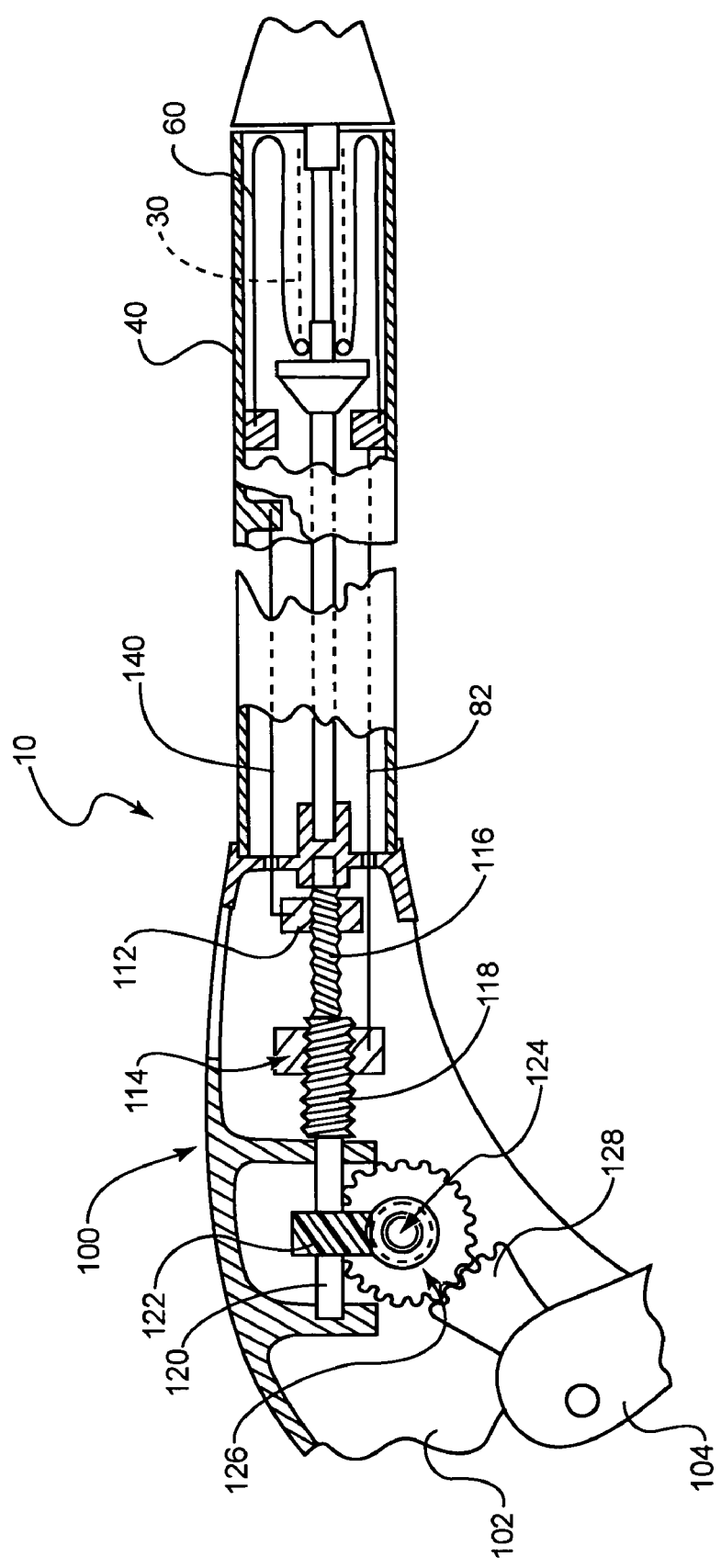
FIG. 9 is a detailed view of a portion of the system shown in FIG. 8.
Figure 10:
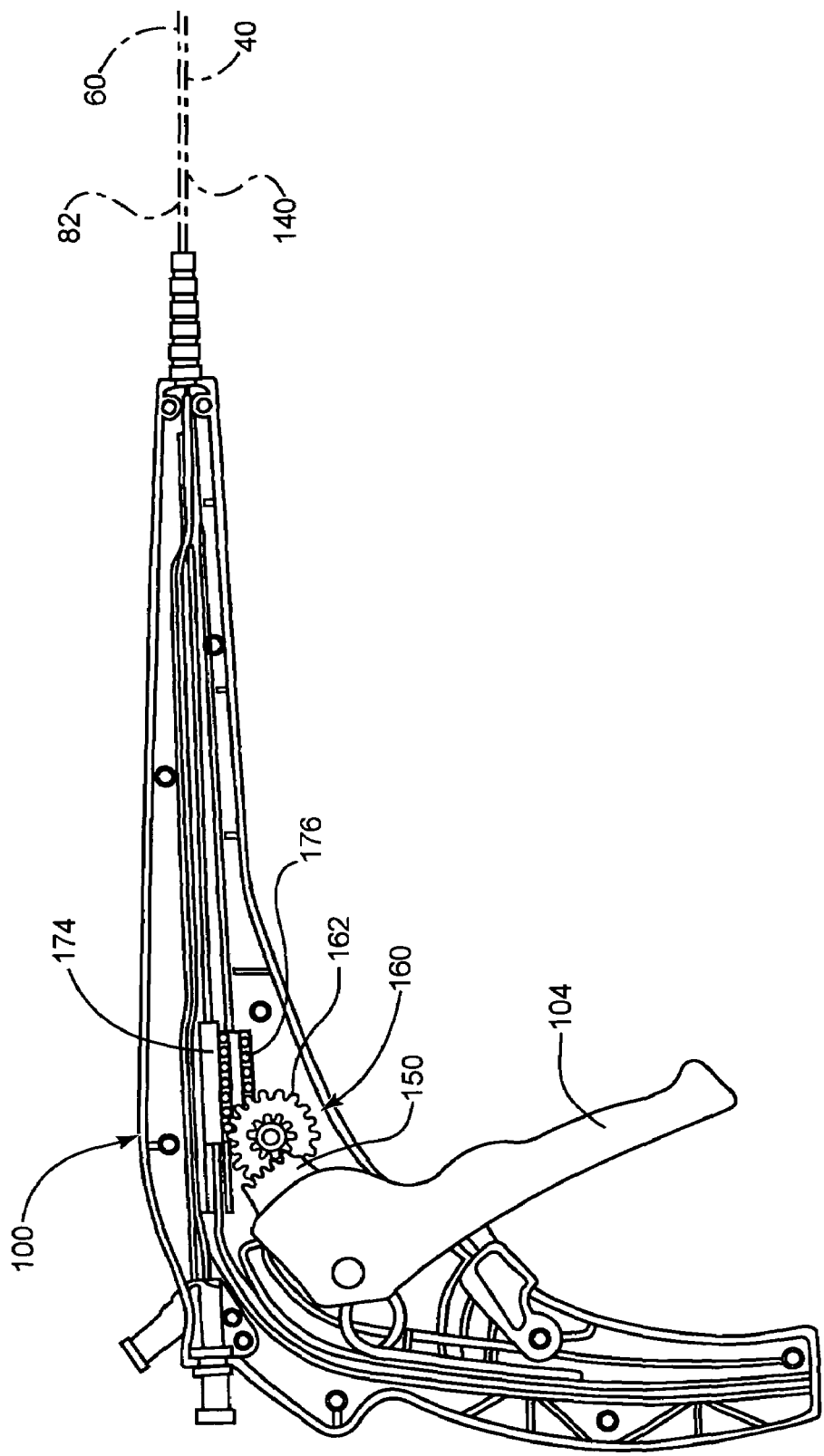
FIG. 10 is partial cross-sectional side view of an alternative retraction mechanism to that shown in FIG. 8.

As is shown in FIGS. 1 and 2, a pull back wire or other member 82 extends proximally from the retraction collar 80 to a retraction mechanism such as the type of retraction mechanisms shown in FIGS. 8-10. The member 82 passes through an opening 86 in the retaining sheath 40 and into a lumen 84 defined by the catheter 10 to where it is engaged to the retraction mechanism 100. When the retaining sheath 40 and the retraction collar 80 are retracted, the retraction collar 80 is slid proximally toward the opening 86. When the retraction collar is slid to or distally adjacent from the opening, the membrane 60 will be withdrawn from about the stent 30, such as in the manner depicted in FIGS. 4-6. When fully withdrawn from about the stent 30, the stent is free to expand to its deployed diameter within a body lumen such as in the manner shown in FIG. 6.

When the retaining sheath 40 and the membrane 60, via retraction collar 80 and pull back member 82, are retracted from about the stent 30, the sheath 40 membrane 60 are withdrawn at different rates to ensure a constant linear relationship between the rolling end of the membrane 60 and the distal end 42 of the retaining sheath 40. In some embodiments the membrane 60 is retracted at a rate twice that of the retraction rate of the retaining sheath 40.

The retraction of the retaining sheath 40 and membrane 60 results in a "peel-back" effect of the membrane 60 to uncover the stent while protecting the coating 50 from detrimental contact from the retaining sheath 40. In some embodiments, an example of which is shown in FIGS. 1 and 2, one or more lubricants 90, may be positioned between the stent 30 and the membrane 60 to further enhance the retraction characteristics of the membrane 60 and discourage disturbances to the coating 50 on the stent 30. In some embodiments a lubricious coating may be applied elsewhere on the catheter 10, such as for example between the retaining sheath 40 and the membrane 60, and/or other locations as desired. Lubricant 90 may be one or more of a variety of lubricious substances such as: hydrogels, silicone, PDMS (polydimethylsiloxane), one or more release agents and any combinations thereof. Some examples of suitable commercially available lubricants include, but are not limited to BIOSLIDE™, GLIDEX™, HYDROPASS™, and MEDIGLIDE™.

Figure 7:
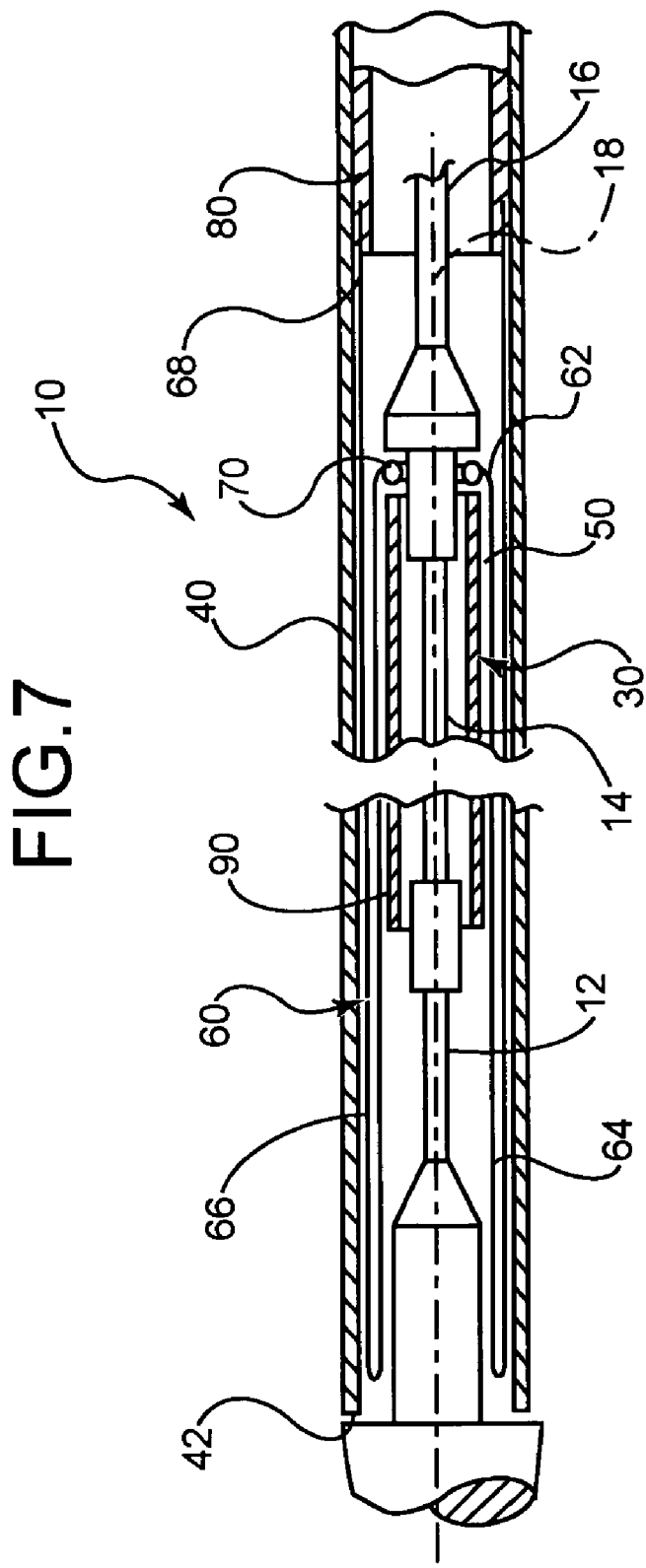
FIG. 7 is a partial cross-sectional side view of an embodiment of the invention comprising a stent delivery system having a rolling membrane.

In at least one embodiment of the invention, an example of which is depicted in FIG. 7, the retaining sheath 40 is positioned external to both the inner region 64 and the outer region 66 of the membrane 60. The second end 68 of the membrane terminates at a retraction collar 80 which is disposed about the inner shaft 12 and within the retaining sheath 40.

An example of a retraction mechanism suitable for use with the assembly depicted in FIG. 7 is shown in FIGS. 8-10, wherein the catheter 10 may be provided with a retraction mechanism 100 which provides for the desired differential rates of retraction of the sheath 40 and membrane 60 with the actuation of a single mechanism, such as trigger 104. It should be noted however, that the various retraction mechanisms described herein may be modified for use with any of the stent delivery configurations shown in FIGS. 1-7.

As previously described, the membrane 60 extends proximally to the retraction collar 80, which in turn is engaged to a pull back member 82. In the embodiment shown in FIGS. 8 and 9, the pullback member 82 extends distally to the retraction mechanism 100 where it terminates at nut 114. In a similar manner, the outer retractable sheath 40 extends proximally to an actuating wire 140, the actuating wire 140, terminates at a sheath retraction member or nut 112. Nut 112 is engaged to a distal thread screw 116 and nut 114 is engaged to a proximal thread screw 118. As is most clearly shown in FIG. 9, the sizes of the screws 116 and 118 are selected so that when the screws are rotated at a similar rate, the nuts 112 and 114 engaged respectively thereto, are drawn proximally at different rates. As indicated above, preferably nut 112 moves at a rate which is about half that of nut 114.

In at least one embodiment the distal screw 116 is characterized as an M3×0.5 (ie. About 3 mm diameter ×about 0.5 mm diameter screw pitch): and proximal screw 118 is a M6×1.0. In at least one embodiment distal screw 116 is M2×0.4 and proximal screw 118 is M5×0.8. As indicated in the various embodiments the pitch of the distal screw 116 is about half that of the proximal screw to provide the desired pull ration of 2:1 in the membrane 60 verses the sheath 40. In some embodiments, variances in the 2:1 ratio may be accommodated.

In embodiments wherein the stent being delivered is particularly long, such as a stent having a length of 60 mm or more, two-start screw threads with significantly larger pitches may be appropriately used as screws 116 and 118.

Rotation of the screws 116 and 118 is accomplished by rotation of a driveshaft 120 about which the screws 116 and 118 are mounted. Along the driveshaft 120, proximal of the screws 116 and 118, a worm wheel 122 is positioned about the driveshaft 120 and is fixedly engaged thereto. The worm wheel 122 is in movable communication with a worm gear 124, such that when the worm gear 124 is rotated the movement of the gear causes the rotation of the worm wheel 122 and the drive shaft 120. The worm gear 124 is also in movable communication with a drive spur 126, which is in movable communication with a segment pinion 128, which is engaged to the trigger 104 within the handle 102 of the retraction mechanism 100. As a result of the above, when the trigger 104 is pivotally actuated relative to the handle 102, the segment pinion 128 is moved. Movement of the segment pinion 128 results in rotation of the drive spur 126 and worm gear 124 and as a consequence the worm wheel 122. By this mechanism the screws 116 and 118 are rotated causing the nuts 112 and 114 to be drawn proximally at different rates resulting in the retraction of the sheath 40 and membrane 60 as desired.

In at least one embodiment the worm wheel 122 and/or drive shaft 120 includes a ratchet mechanism so that the worm wheel 122 only rotates in a single direction which matches the 'hand' of the screws.

Figure 11:
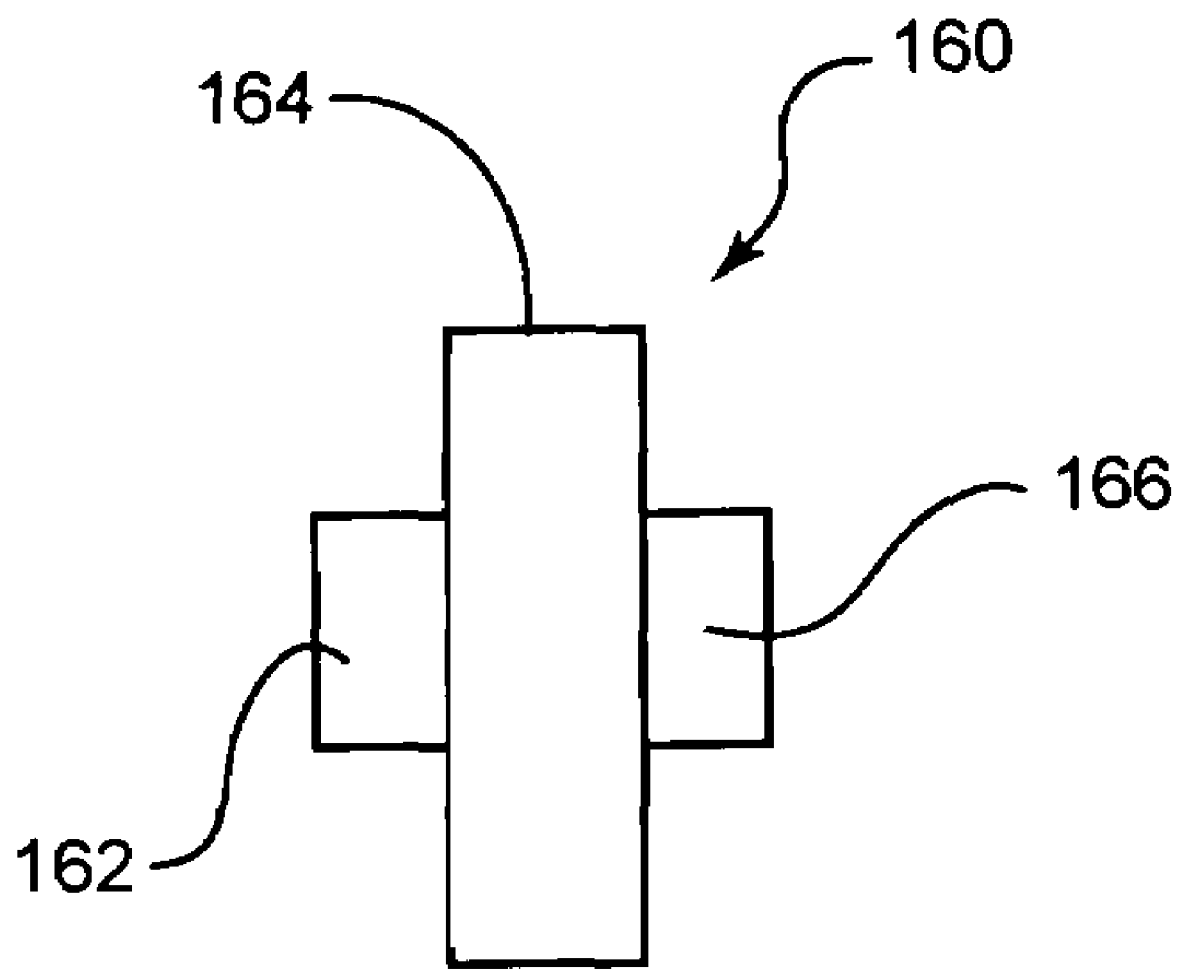
FIG. 11 is a detailed frontal view of the triple pinion depicted in FIG. 10.

Other retraction mechanisms may also be provided which result in the desired differential pull back rates for the sheath 40 and membrane 60. For example, in the embodiment shown in FIG. 10, a retraction device 100 is shown which includes a triple pinion system for retracting the sheath 40 and membrane 60. In the retraction mechanism 100 shown, the trigger 104 is engaged to a segment gear 150. The segment gear 150 is in moveable communication with a first pinion 162 of a triple pinion 160. As is shown in FIG. 11, the triple pinion 160 includes the first pinion 162 as well as a second pinion 164 and a third pinion 166. In use, when the first pinion 162 is rotated as a result of the actuation of the trigger 104 and segment gear 150, the second pinion 164 and third pinion 166 are also rotated.

As is shown in FIG. 10, the second pinion 164 is moveably engaged to a membrane pull back strip 174 and the third pinion 166 is moveably engaged to a sheath pull back strip 176. The pull back member 82 of the membrane proximally terminates at the membrane pull back strip 174 and the actuating wire 140 of the retractable sheath 40 terminates at the sheath pull back strip 176. As a result of the different sizes of the second pinion 164 and third pinion 166 when the triple pinion 160 is rotated as a result of trigger actuation, the strips 174 and 176 are proximally retracted at different rates. The desired differential pull back rates may be accomplished by providing the second pinion 164 with the same size, but twice the number of 'teeth' as the third pinion 166.

It is recognized that retraction mechanisms other than just those described above may be utilized to provide the retraction/pullback characteristics necessary to retract the sheath and membrane to release the stent for delivery.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device for delivery of a self-expanding stent comprising:
   a catheter having a catheter shaft, a self-expanding stent disposed about a stent receiving region of the catheter shaft;
   a retractable sheath disposed about the catheter shaft and the stent, the retractable sheath having an internal surface and an external surface; and
   a retractable membrane, prior to delivery of the stent a first portion of the retractable membrane being positioned between the stent and the inner surface of the retractable sheath, a second portion of the retractable membrane extends from the first portion and along the external surface of the retractable sheath, the retractable sheath and the retractable membrane being independently moveable relative to one another.

2. The medical device of claim 1 wherein at least a portion of the stent is coated with at least one therapeutic agent.

3. The medical device of claim 2 wherein the at least one therapeutic agent comprises at least one drug.

4. The medical device of claim 1 wherein the retractable membrane comprises a first end, the first end being fixedly engaged to a portion of the catheter shaft proximal to the stent receiving region.

5. The medical device of claim 4 further comprising a retaining collar, the retaining collar fixedly retaining the first end of the membrane to the catheter shaft.

6. The medical device of claim 4 wherein the first portion of the retractable membrane extends distally from the first end to a distal end of the retractable sheath, the retractable membrane being wrapped around the distal end of the retractable sheath.

7. The medical device of claim 6 wherein the second portion of the retractable membrane extends proximally from the distal end of the retractable sheath to a second end of the retractable membrane.

8. The medical device of claim 7 wherein the second end of the retractable membrane is fixedly engaged to a retraction collar, the retraction collar being disposed about a portion of the retractable sheath and independently slideable relative thereto.

9. The medical device of claim 8 further comprising a retraction member, the retraction member being engaged to the retraction collar and extending proximally therefrom.

10. The medical device of claim 9 wherein the retractable sheath defines an opening therethrough, the retraction sheath and the catheter shaft defining a lumen therebetween, the opening being in communication with the lumen, the retraction member extending through the opening and into the lumen.

11. The medical device of claim 1 wherein the retractable membrane is constructed of a polymer of at least one member of the group consisting of polyester, polyamide, polyethylene terephalate polyester, crosslinked polyethylene, polyurethane, plasticized polyvinylchloride, polytetrafluoroethylene, and any combination thereof.

12. The medical device of claim 1 wherein the retractable membrane comprises a plurality of separate strips of membrane material.

13. The medical device of claim 1 wherein the retractable sheath is constructed of at least one sheath material and the retractable membrane is constructed of at least one membrane material, wherein the at least one sheath material is more rigid than the at least one membrane material.

14. The medical device of claim 1 further comprising a lubricant, the lubricant positioned on at least a portion of the retractable membrane.

15. The medical device of claim 14 wherein the lubricant is selected from at least one member of the group consisting of: hydrogels, silicone and polydimethylsiloxane.

16. The medical device of claim 1 further comprising a retraction device, the retraction device, the retraction device being actuatable between a non-retracted position and a retracted position, wherein in the retracted position the retractable sheath and the retractable membrane are retracted from about the stent.

17. The medical device of claim 16 wherein the retraction device comprises a first mechanism and a second mechanism, the first mechanism operably engaged to the retractable sheath, the second mechanism operably engaged to the retractable membrane, wherein actuation of the retraction device causes the second mechanism to provide the retractable membrane with a rate of retraction from the stent about twice that of the rate provided by the first mechanism to the retractable sheath from the stent.

18. The medical device of claim 17 wherein the retraction device comprises a screw drive.

19. The medical device of claim 17 wherein the retraction device comprises a triple pinion.

20. A medical device for delivery of a self-expanding stent comprising:
   a catheter, the catheter having a catheter shaft, a portion of the catheter shaft defining a stent receiving region;
   a self-expanding stent, the stent being expandable from a reduced state to an expanded state, in the reduced state the stent having a diameter less than the diameter in the expanded state;
   a retaining sheath, the retaining sheath being disposed about the catheter shaft and being longitudinally moveable relative thereto, the retaining sheath being moveable between a retaining position and a withdrawn position, in the retaining position the a portion of the retaining region being disposed about the stent receiving region and retaining the stent in the reduced state, in the withdrawn position the sheath being removed from the stent receiving region; and a rolling membrane, the rolling membrane being moveable from a covered configuration to a withdrawn configuration, the rolling membrane having a first end, a second end and inside region and an outside region, the first end being fixedly engaged to a portion of the catheter shaft proximal to the stent receiving region, the inside region positioned between the catheter shaft and the retaining sheath and extending distally from the first end to a distal end of the retaining sheath, the outside region extending to the second end external of the retaining sheath, the outside region extending proximally from the inside region, the second end being engaged to a retraction member, in the covered configuration the inside region positioned between the stent and the retaining sheath, in the withdrawn configuration the rolling membrane being withdrawn from about the stent.

* * * * *